May 29, 1956 T. E. MOTOSE Plant Pat. 1,480
ROSE PLANT
Filed June 21, 1955
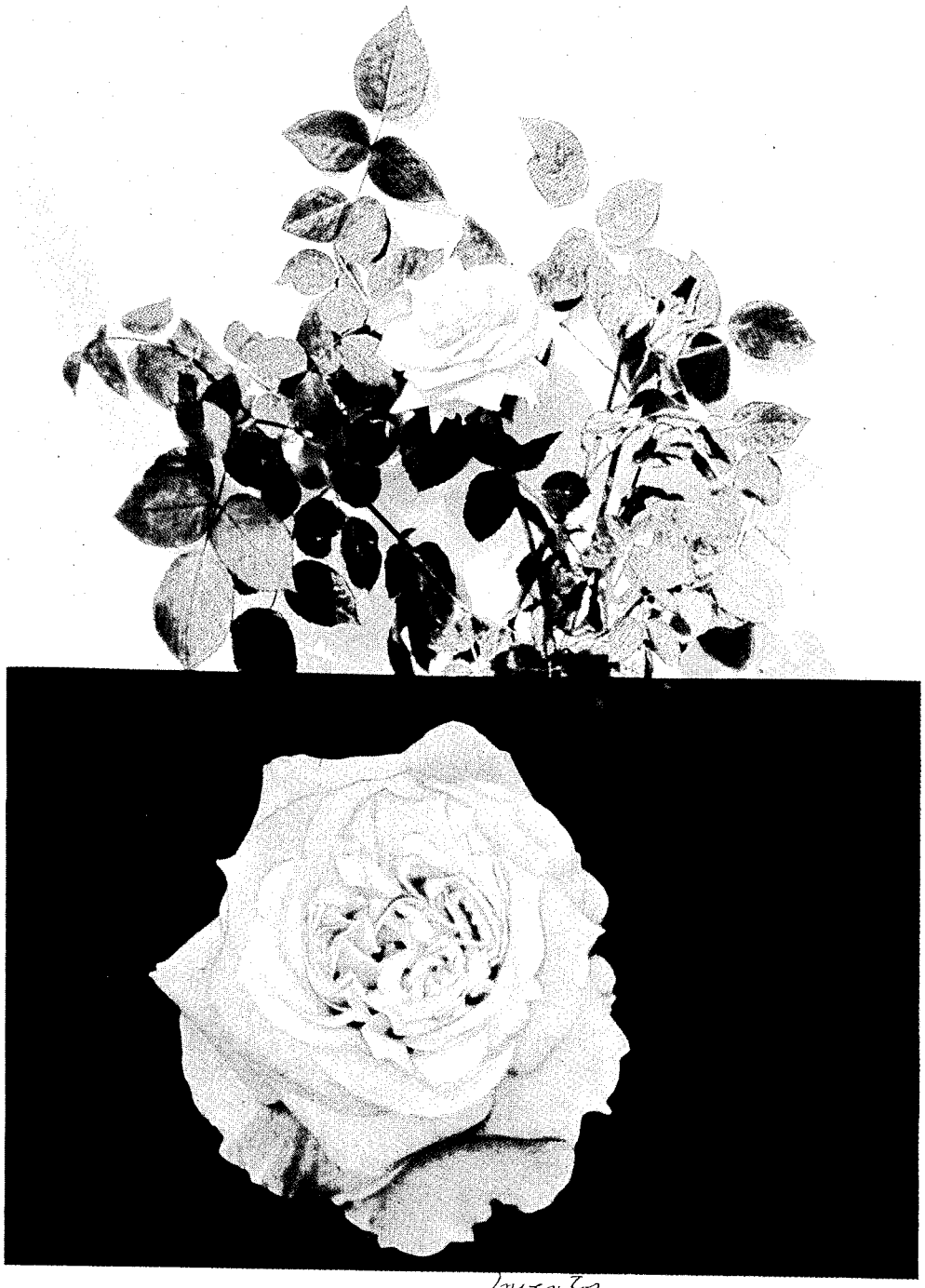
Inventor
Thomas Edison Motose United States Patent Office Plant Pat. 1,480
Patented May 29, 1956

1,480

ROSE PLANT

Thomas Edison Motose, Fairport, N. Y.

Application June 21, 1955, Serial No. 517,097

1 Claim. (Cl. 47—61)

The present invention relates to a new and distinct variety of hybrid tea rose, originating as a cross between the known variety Neige Parfum (a hybrid tea bearing large, fragrant white blooms, introduced in 1939 by A. Meilland but not patented) and a seedling which was a cross of Charlotte Armstrong (a hybrid tea rose bearing large, spectrum-red to cerise flowers, Plant Patent 455) and Blanche Mallerin (a hybrid tea rose with large white blooms, Plant Patent 594).

The parent varieties are very vigorous in growth and have very good blooming characteristics, i. e., great frequency and large quantity of blooms.

The said Neige Parfum and the said seedling were crossed for the purpose of producing a rose plant that shall bear blooms resembling those of the peony in general floral pattern, with a minimum of the conventional rose form, and that shall have very good blooming characteristics and vigor in growth.

Since the average garden peony grown in the United States is a once-a-year bloomer and the hybrid tea a repeating bloomer, the present invention is useful in the sense that it reminds us of, and in some measures substitutes, the peony during the many months when the latter is not in flower.

The following characteristics, considered as a "combination," constitute the distinguishing features of this new variety and set it apart from all the other varieties known to me:

(1) Recurrent or continuous blooming habit.

(2) Vigorous and fast growing canes and branches.

(3) Flower resembling that of the peony in general pattern, with (*a*) Large, slightly waved, white (faintly overcast with pink) petals arranged evenly on the outer side;

(*b*) Smaller, ovate, cream-colored (tinted pink on the outer edge) petals arranged evenly, and sometimes unevenly, next to the row of outer petals; and (*c*) Ovate, lanceolate and irregularly shaped pink petaloids arranged in one roundish cluster towards and in the center.

(4) Long lasting quality of the bloom rivaling the life-span of the average bloom of hybrid polyantha roses.

(5) Bloom attaining its most beautiful stage when fully opened and not very pretty when partly opened—a phenomenon that is a reverse of the average hybrid tea rose.

The above distinguishing characteristics, and the combination thereof, of the new variety have been found to be established definitely and to hold true through succeeding asexual propagations or reproductions. Buddings, cuttings, and graftings of the new variety were successfully performed in Fairport, N. Y.

The accompanying photograph of the new variety shows the forms and colors of the various parts of the plant. The most important differentiating part of the new variety is the flower and this is specially enlarged in the photograph to show its details. There is very little or no differentiating feature in the very young leaves, young buds and unopened buds.

The place where, and the time when, observations made for the specific purpose of compiling data for this specification: Fairport, N. Y., September 1954.

The colors of the various parts of this new variety, mentioned in the foregoing and to be described in detail in the pages to follow, are those observed in an outdoor garden in fair weather during the early part of September, 1954, in Fairport, N. Y. In common with those of other rose blooms, the color of bloom of this new variety is subject to the influences of sun, chemical fertilizers, soil and seasonal conditions, and its pink coloring may undergo slight changes in intensity from time to time.

The following is a detailed description of this new variety, with color terminology in accordance to Ridgway's Color Standard and Nomenclature (when plate number is given) or in accordance to the generally accepted meaning of Webster's Standard Dictionary (when no plate number is given):

(1) *Parentage*

A seedling of a pollen parent named Neige Parfum and an unnamed seed parent, the latter a cross of Charlotte Armstrong and Blanche Mallerin.

(2) *Classification*

*Botanical.*—Hybrid tea.

*Commercial.*—Hybrid tea.

(3) *Plant as a whole*

*Shape.*—Bushy and well branched.

*Growth.*—Vigorous and fast growing.

*Height when fully grown in the climate of northern New York.*—Averaging three and half to four feet.

*Disease resistance.*—Very resistant to black-spots and rusts as observed in test garden in Fairport, N. Y., in which a program of once a week all purpose spraying was followed.

(4) *Canes and stems*

*Older canes.*—Smooth bark, Cress Green (Plate 31) in color.

*Younger canes.*—Smooth bark, Hay's Russet (Plate 14) in color.

*Very young shoots.*—Light Elm Green (Plate 17) with the very tender tips touched with Oxblood Red and occasionally pinkish hue.

*Thorns.*—Average in quantity, very sharp pointed and growing out in right angle to the cane, thin and small in size, light ivory overcast with pink when young and dull ivory without the pinkish overcast when old.

(5) *Foliage*

*Quantity.*—Abundant.

*Size of leaf.*—Large.

*Number of leaflets in an average leaf.*—Five as a rule. Occasionally, the leaf may consist of 3 or 7 leaflets.

*Shape of leaflets.*—Oval pointed.

*Texture.* — Upper side—slightly leathery and unwrinkled; under side—slightly leathery and unwrinkled.

*Ribs and veins.*—Well marked, and sometimes very conspicuous.

*Serration of edge.*—Single as a rule, occasionally multiple, clearly marked and evenly spaced as a rule.

*Leaf stem.*—Absinthe Green (Plate 31) in color with few prickles underneath.

*Stipules.*—Medium length, Absinthe Green (Plate 31).

*Color of mature leaf.*—Upper side—Forest Green (Plate 17); under side—Light Bice Green (Plate 17).

*Color of young leaf fully opened.*—Upper side—Oil Green (Plate 5) with overcast of Oxblood Red (Plate 1) and sometimes with pinkish overcast; under side—Yellowish Oil Green (Plate 5) with overcast of Oxblood Red (Plate 1) as a rule, and occasionally with pink.

*Color of very young leaf still folded.*—Various degrees of green (depending upon weather conditions) with a generous shading of Oxblood Red (Plate 1).

(6) *Flower bud*

*Size.*—Large.

*Shape.*—Ovoid before sepals separate.

*Tendency.*—Sepals separate before the petals are mature enough to unfurl.

*Sepals.*—Slightly serrated, Biscay Green (Plate 17) in color inside, Light Bice Green (Plate 17) outside.

*Calyx.*—Large in size; Biscay Green (Plate 17) in color.

*Peduncle.*—Large, stiff and smooth; Biscay Green (Plate 17) in color.

*Colors of visible parts of petal when sepals begin to divide but not fully separated.*—Coral Pink (Plate XIII) towards the tip, and Pale Pinkish Buff (Plate XXIX) towards the base.

*Colors of visible parts of petal when sepals are fully separated and before the petals are unfurled.*—Light Coral Red (Plate XIII) towards the tip, Flesh Color (Plate XIV) midway, Pale Pinkish Buff (Plate XXIX) towards the base.

(7) *Flower*

*Opening.*—Opens up slowly but surely, and does not "ball" (a condition in which the bloom remains in a ball shape without the petals unfurling outward) in most weather conditions.

*Speed in opening.*—After the complete separation of sepals, the petals unfurl slowly taking from three to five days to open fully, and frequently longer.

*Life span.*—Long lasting on the bush, longevity comparable to that of hybrid polyantha class of roses.

*Size.*—Large, 5 to 6 inches in diameter.

*Borne.*—Singly, rarely in multiple, on strong stem.

*Form.*—Slightly cupped when first opened and flattens out when fully unfurled, but with slight prominence in the center area, resembling in general pattern and size those of the average peony bloom.

*Petalage.*—Very double, 50 to 60 (counting the petaloids) under normal weather condition, the outer petals being very large and the inner petals small.

*Color of outer area viewed from above.*—White (Plate 53) overcast with very light pink resembling the light pinkness of the Baldwin's apple blossom at its prime.

*Color of intermediate area viewed from above.*—White (Plate 53) lightly overcast with Cameo Pink (Plate 26), with the outer edges of most of the petals tinted with solid Cameo Pink (Plate 26) without an overcast.

*Color of central area viewed from above.*—Cameo Pink (Plate 26) without white or overcast.

*General color of a fully opened blossom viewed from a distance.*—White peony bloom with pink center.

*Discoloration.*—The outer area remains white, while the central area gradually turns to apple blossom color after about a week of bloom in normal Fairport, N. Y., weather when the temperature of the growing season is not too extreme.

*Fragrance.*—Very sweet old rose scent.

*Most beautiful stage.*—Attains its most beautiful stage when fully opened, which fact is one of the important differentiating features which distinguish this new variety and its sisters from the majority of other hybrid tea roses which usually attain their greatest beauty when they are partly opened.

(8) *Petals*

*Outer.*—Large, almost heart-shape, waved at outer edge, a small dentation (projection from the general margin) on the free outer edge or apex of some petals and one or more large but irregular indentations (cut or notch) on the free outer edge or apex of others, White (Plate 53) lightly overcast with apple blossom pink on both surfaces with a small area of Lemon Yellow (Plate IV) at the base.

*Intermediate.*—Medium, some heart-shaped and some ovoid, outer edge unwrinkled, a well defined dentation (projection from the general curved margin) found frequently on the free outer edge or apex, White (Plate 53) overcast with Cameo Pink (Plate 26) on both surfaces except the outer edge, solid Cameo Pink (Plate 26) on both surfaces of outer edge or apex and dentation (this pink border, measuring about one-eighth to one-fourth of an inch in width and encircling almost all the visible edge, merges gradually with and into the white area).

*Central.*—Small, irregular shapes, irregular indentations and dentations on free outer edges, all Cameo Pink (Plate 26).

*Texture.*—Smooth and thick.

*Appearance.*—Satiny (both surfaces).

*Arrangement.*—Imbricated (larger petals), irregular (smaller petals).

*Persistence.*—Drop off cleanly in normal weather condition prevailing during growing season in Fairport, N. Y.

*Minor peculiarity.*—The Cameo Pink (plate 26) colored area appearing as a narrow outer border of the intermediate petals occasionally appears on outer petal or petals.

(9) *Genital organs*

*The genital organs.*—Hidden by petaloids as a rule.

*Anthers.*—Medium in size, few in number, Light Orange Yellow (Plate 3) and often lighter yellow in color.

*Filaments.*—Short in length, Sulphur Yellow (Plate 5) in color.

*Pollen.*—Yellow Orange (Plate 3) in color; few.

*Styles.*—Uneven and short; light yellow.

*Stigmas.*—Medium in size; various shades of red (often Morocco Red, Plate I) on the upper end or section except the orifice, and various shades of light yellow around the orifice.

*Ovaries.*—Normally enclosed in calyx.

(10) *Growth*

Vigorous and fast growing as seen in New York State.

(11) *Hardiness*

Lives through winter without difficulty in outdoor garden of Fairport, N. Y., with little or no protective coverings of added soil or straws.

(12) *Flowering habit*

Recurrent, continuous.

I claim:

A new and distinct variety of rose plant of the hybrid tea class, characterized as to novelty by the color combination, shape and long lasting quality, of its bloom, the capacity or tendency of its flowers to attain their fullest or greatest beauty when their petals are fully unfurled, its prolific and recurrent blooming habit and the vigor of its growth and hardiness, substantially as described herein and also shown in the accompanying colored photograph.

No references cited.